(12) United States Patent
Harvey

(10) Patent No.: US 7,638,545 B1
(45) Date of Patent: Dec. 29, 2009

(54) ANTHELMINTIC COMPOSITION

(75) Inventor: Colin Manson Harvey, Auckland (NZ)

(73) Assignee: Merial Limited, Duluth, GA (US)

( * ) Notice: Subject to any disclaimer, the term of this patent is extended or adjusted under 35 U.S.C. 154(b) by 0 days.

(21) Appl. No.: 09/958,814

(22) PCT Filed: Apr. 14, 2000

(86) PCT No.: PCT/NZ00/00053

§ 371 (c)(1),
(2), (4) Date: Jan. 8, 2002

(87) PCT Pub. No.: WO00/61068

PCT Pub. Date: Oct. 19, 2000

(30) Foreign Application Priority Data

Apr. 14, 1999 (NZ) ...................... 335166

(51) Int. Cl.
*A01N 43/52* (2006.01)
*A01N 43/04* (2006.01)
*A01N 31/00* (2006.01)

(52) U.S. Cl. .................. 514/394; 514/30; 514/395; 514/724

(58) Field of Classification Search ............ 514/394, 514/395, 30, 724
See application file for complete search history.

(56) References Cited

U.S. PATENT DOCUMENTS

| | | | | |
|---|---|---|---|---|
| 4,144,352 A * | 3/1979 | Putter | ............. | 514/450 |
| 4,197,307 A | 4/1980 | Gallay et al. | | |
| 4,672,072 A * | 6/1987 | Hackney et al. | ............. | 514/368 |
| 5,459,155 A | 10/1995 | Banks et al. | | |
| 5,468,765 A | 11/1995 | Banks et al. | | |
| 5,744,494 A * | 4/1998 | McKellar et al. | ............. | 514/388 |
| 5,840,324 A | 11/1998 | Hennessy et al. | | |
| 5,861,142 A * | 1/1999 | Schick | ............. | 424/61 |
| 5,925,374 A | 7/1999 | McLaren et al. | | |
| 6,013,636 A * | 1/2000 | Harvey | ............. | 514/30 |
| 6,165,987 A * | 12/2000 | Harvey | ............. | 514/30 |
| 6,340,672 B1 * | 1/2002 | Mihalik | ............. | 514/30 |
| 6,492,340 B2 * | 12/2002 | Mihalik | ............. | 514/30 |

FOREIGN PATENT DOCUMENTS

| | | |
|---|---|---|
| AU | 31278/84 | 2/1985 |
| AU | 31358/84 | 2/1985 |
| EP | 045655 | 8/1981 |
| EP | 146414 | 12/1984 |
| FR | 2755824 | 5/1998 |
| GB | 1527584 | 4/1977 |
| NZ | 186936 | 4/1978 |
| NZ | 208992 | 7/1984 |
| NZ | 209100 | 8/1984 |
| NZ | 199817 | 12/1984 |
| NZ | 235647 | 10/1990 |
| NZ | 261137 | 2/1994 |
| NZ | 330005 | 3/1998 |
| NZ | 329247 | 8/2000 |
| WO | WO 94/27598 | 12/1994 |
| WO | WO 01/60380 | 2/2001 |

OTHER PUBLICATIONS

Bennett et al., *Experimental Parasitology*, "Fasciola hepatica: Action in vitro Trilabendazole on Immature and Adult Stages", pp. 49-57.

Fetterer, R.H., *Journal of Veterinary Pharmacology and therapeutics*, "The effect if albendazole and triclabendazole on colchicine binding in the liver fluke", pp. 49-54.

Shoop et al., Structure and activity of avermectins and milbemycins in animal health, Veterinary Parasitology 1995, 59, 139-156.

McKellar & Benchaoui, Avermectins and milbemycins, .J. vet. Pharmacol. Therap. 1996, 19, 331-351.

* cited by examiner

*Primary Examiner*—Kevin E Weddington
(74) *Attorney, Agent, or Firm*—Judy Jarecki-Black; Thomas Kowalski, Esq.; Merial Limited

(57) ABSTRACT

A formulation having triclabendazole in solution. In addition a further anthelmintic may be included. The formulation is made by mixing the abamectin and benzyl alcohol and mixing this with triclabendazole and butyl dioxitol. The mix is then heated to dissolve the active, and allowed to cool at which stage the solution is diluted to volume with PEG 4000.

27 Claims, No Drawings

ANTHELMINTIC COMPOSITION

FIELD OF THE INVENTION

This invention relates to novel anthelmintic formulations and in particular it relates to stable veterinary formulations containing the anthelmintic triclabendazole.

BACKGROUND

The benzimidazoles, including triclabendazole, are well known for their anthelmintic activity. Of all the benzimidazoles known, triclabendazole is particularly useful, as it is highly effective against liver flukes at all stages of their life cycle. Albendazole, in contrast, is only effective against adult flukes.

Triclabendazole, is also known as 5-Chloro-6(2,3-dichlorophenoxy)-2-methylthio-1H-benzimidazole, and represented by Formula I.

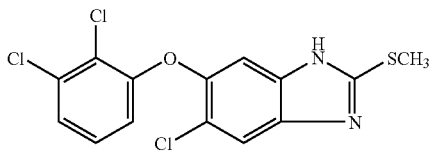

Ruminants, such as sheep, cattle and goats, are susceptible to *Fasciola*, the disease caused by parasitic liver flukes, and it is important that formulations effective against the disease are available. In particular it is advantageous to have liquid formulations which contain the active anthelmintic in solution and which are easily administered by way of a pour-on.

It has been difficult to provide liquid formulations containing triclabendazole due to the highly insoluble nature of the compound. This has resulted in anthelmintic formulations containing triclabendazole being prepared as suspensions. Suspension formulations have a number of disadvantages. The most serious relates to stability. Veterinary formulations may be stored for extended periods in large, opaque containers and must be stable. Suspensions tend to be unstable in that the actives tend to settle out of the formulation. This causes problems as it results in differences in concentration of the active through the formulation. This is turn leads to difficulties in determining the effective and safe doses for treatment of livestock. Suspensions are also less able to be absorbed when applied by way of a pour-on. Pour-ons must be formulated to penetrate the skin which is the body's natural barrier. While a suspension may be absorbed from the digestive tract the same formulation applied to the skin would be less able to be absorbed. By developing suitable liquid formulations particularly with solvents which have a good affinity for penetrating skin the active is more likely to be absorbed. With most actives applied as pour-ons to the dermis the dose rate at which it is applied is increased when compared to an oral or injectable formulation. This is to make up for the less efficient absorption through skin tissues.

OBJECT

It is an object of the invention to provide an improved stable liquid anthelmintic solution containing an effective amount of triclabendazole which is suitable for administration to warm blooded animals or one which at least provides the public with a useful choice.

STATEMENT OF INVENTION

In one aspect the invention provides a stable liquid veterinary formulation containing an effective amount of triclabendazole wherein the triclabendazole is dissolved in at least one solvent.

Preferably the invention relates to a stable liquid veterinary formulation suitable for administration by pour-on.

Preferably the solvent is selected from the group including benzyl alcohol, glycerol formal, n-methyl-2-pyrrolidone, glycol ethers such as butyl dioxitol (also known as Dipropylene glycol mether ether) and related isomers and aromatic solvents such as xylene or toluene.

Most preferably the solvent is at least one of benzyl alcohol and glycerol formal.

More preferably the stable liquid veterinary pour-on formulation includes triclabendazole present in the range 10-40% w/v.

Preferably the formulation may include at least one additional anthelmintic selected from the group avermectins, milbemycins, tetramisole and levamisole, which is soluble in the pour-on formulation of this present invention.

Most preferably the additional anthelmintic is selected from the avermectins.

Most preferably avermectin is also present in the range 0.25-2% w/v.

In another related aspect the invention relates to a method of treating warm blooded animals for parasites by administering to said animal a formulation of the present invention.

In another related aspect the invention relates to a method of treating liver flukes in warm blooded animals by administration of pour-on formulation.

PREFERRED EMBODIMENTS

It has now been found that stable liquid formulations containing the active triclabendazole in solution can be prepared and that these actives can be absorbed through the skin to control the infection of liver in animals in particular cattle.

The above, and other aspects of the invention, which should be considered in all its novel aspects will be apparent from the following examples.

EXAMPLE 1

The formulation of this example is shown in table 1. It is suitable for administration as a pour-on, in particular to cattle. The recommended dose rate is:

TABLE 1

| INGREDIENT | g/100 mL |
|---|---|
| Abamectin | 0.5 |
| Triclabendazole | 30.0 |
| Butyl dioxitol | 50.0 |
| Benzyl Alcohol | 5.0 |
| PEG 400 | to volume |

To prepare the formulation add the abamectin and benzyl alcohol. To this add butyl dioxitol and the triclabendazole. Warm to 40° C. and stir to dissolve. Cool mix to less than 25° C. and dilute to volume with PEG 400. It will be apparent to the skilled addressee if filtering is necessary at this point.

Trials

Stability Trials

A stability trial was conducted to ensure that the triclabendazole solution was stable. A formulation made as described in example 1 ("Formulation 1") was stored at ambient for 11 months. At the conclusion of the storage period samples were tested for total abamectin and triclabendazole levels. The results are presented in table 2 below.

TABLE 2

Stability Trial Formulation 1

| | Abamectin B1$_a$ | Abamectin B1$_b$ | Total Abamectin | Triclabendazole |
|---|---|---|---|---|
| Date of manufacture Day 1 | 0.48 | 0.02 | 0.50 | 31.3 |
| End of trial Day 345 | 0.48 | 0.008 | 0.49 | 28.9 |

| Method | Reference | Technique |
|---|---|---|
| Abamectin | H127/01V3 | HPLC |
| Triclabendazole | In House | HPLC |

The results clearly show that the triclabendazole remained in solution. There was no loss in activity for either abamectin or triclabendazole.

Efficacy Trials

Trials were conducted comparing the efficacy of the Formulation 1 with two other treatments and a control. The trial included twenty animals all confirmed infected with *Fasciola* spp. The animals were divided into four groups of five animals. The animals were ranked on the basis of faecal fluke egg counts, and divided into blocks of four. Animals from each block were randomly allocated to one of the four treatment groups. Egg counts were performed twice on animals a week prior to the trial to confirm all animals had a *Fasciola* spp burden. At day zero of the trial all animals were treated according to the protocol set out in Table 3. Group 1 animals were left untreated as controls. Group 2 received Formulation 1. Group 3 were the positive control group and received a commercial flukacide Fasinex 50 (Novartis). Group 4 received triclabendazole oral formulations at levels shown in table 3. During the course of the trial all animals were grazed as a single group grazing on fluke infested pastures up to treatment and then removed to fluke free pastures post treatment.

TABLE 3

Group 1 No treatment
Group 2 At 5 ml per 50 kg topically with the pour-on of Formulation 1
Group 3 At 12 ml per 50 kg orally with Fasinex 50 50 mg per ml of triclabendazole
Group 4 At 12 ml per 50 kg orally with the triclabendazole oral drench containing 50 mg per ml of triclabendazole At 14 days post treatment all animals were sacrificed. Total worm counts were performed using the following procedures:

1. Faecal egg counts
2. *Fasciola hepatica* liver counts. The liver counts were performed by collecting the entire liver (ensuring the gall bladder remained intact) at necropsy. The liver was then labelled and transported (within 4 hours) on ice to laboratory facilities.
3. The liver was laid on a smooth surface and was evaluated for gross pathological changes according to the morbid pathology score sheets.
4. Large bile ducts and gall bladder were dissected allowing the mature and larger immature fluke if present to be seen. These were counted and recorded on sheets. The balance of the liver tissue is dissected into 1 cm thick slices and gently squeezed between the fingers. Any immature fluke appearing from the tissue were retrieved and countered. Remaining tissue was homogenised in a tissue "Stomacher" and washed over a 20 micron mesh such that any remaining immature flukes were recovered. The total worm counts were collated into the treatment groups.

Effective control was obtained against an established natural *Fasciola* hepatica burden with all formulations. The results are summarised on table 4 below.

TABLE 4

Total Worm Counts

| Treatment | | Adult *Fasciola* hepatica | Immature *Fasciola* hepatica |
|---|---|---|---|
| Control | mean | 20 | 4.3 |
| | — | n/a | n/a |
| Formulation 1 | mean | 0 | 0 |
| | % reduction | 100 | 100 |
| Fasinex 50 | mean | 0 | 0 |
| | % reduction | 100 | 100 |
| TCB formulation | mean | 0 | 0 |
| | % reduction | 100 | 100 |

It can be clearly seen from the trials that the formulations of the present invention provide effective treatment of infection by the parasite *Fasciola hepatica*.

In addition the formulations of the present invention provide the advantage of increased stability over the previous suspension formulations.

The combination of increased stability and effective treatment against all stages of *Fasciola hepatica* is a real advantage. It allows the storage of formulation for long periods as may arise in veterinary practises or on the farm eliminating wastage. In addition it eliminates the problems caused by settling of actives. The maintenance of the actives in solution and therefore maintaining a uniform concentration across the formulation ensuring an effective safe dose on application at the recommended dosage.

ADVANTAGES

It is advantageous to be able to provide triclabendazole in stable solutions which can be more easily and effectively administered by pour-on. These solutions also allow the use of triclabendazole in combination with other anthelmintics resulting in broader spectrum of activity, and consequently a reduction in the number of treatments required. Now that triclabendazole can be dissolved to form a stable pour-on solution the opportunities for combining this effective anthelmintic with other actives in stable solutions have substantially increased.

VARIATIONS

It is envisaged that the formulations are the subject of the invention may be modified by the inclusion of additional excipients without departing from the spirit and scope of the invention.

In particular it may be desirable to include dyes in the formulation to allow easy identification of treated animals. Alternately other excipients such as buffers, thickeners, spreading agents may be included to modify the formulation to specific animals.

Finally it will be appreciated that various other alterations and modifications may be made to the foregoing without departing from the scope of the invention.

The invention claimed is:

1. A pour-on formulation comprising a solution of about 30% w/v triclabendazole or its pharmaceutically acceptable salt thereof substantially dissolved in a solvent system;
   about 0.5% w/v abamectin; and
   wherein the solvent system comprises butyl dioxitol; benzyl alcohol; and polyethylene glycol 400.

2. The pour-on formulation according to claim 1, wherein the butyl dioxitol, benzyl alcohol, and polyethylene glycol 400 are in an amount of about 50% w/v; about 5% w/v; and about 14.5% w/v, respectively.

3. A pour-on formulation comprising a solution of at least 20% w/v triclabendazole or its pharmaceutically acceptable salt substantially dissolved in a solvent system, about 0.5% w/v of milbemycin, and wherein the solvent system comprises butyl dioxitol, benzyl alcohol and polyethylene glycol 400.

4. A pour-on formulation comprising triclabendazole in an amount of about 30% w/v or its pharmaceutically acceptable salt substantially dissolved in a solvent system about 0.5% w/v of milbemycin, and wherein the solvent system comprises butyl dioxitol, benzyl alcohol and polyethylene glycol 400.

5. A pour-on formulation comprising a solution of at least 20% w/v triclabendazole or its pharmaceutically acceptable salt substantially dissolved in a solvent system, about 0.5% w/v of abamectin, and wherein the solvent system comprises butyl dioxitol, benzyl alcohol and polyethylene gycol 400.

6. A method of treating parasites in warm-blooded animals comprising administering to said animal in need thereof an effective amount of a pour-on formulation according to any one of claims 1, 2, 3 or 5.

7. A method of treating liver flukes in warm-blooded animals comprising administering to said animal in need thereof an effective amount of a pour-on formulation according to any one of claims 1, 2, 3 or 5.

8. A method of treating fasciolosis in warm-blooded animals comprising administering to said animal in need thereof an effective amount of a pour-on formulation according to any one of claims 1, 2, 3 or 5.

9. The method according to claim 6 wherein said pour-on formulation is administered in a quantity of up to about 50 ml onto the skin surface of said animal.

10. The method according to claim 6 wherein said warm-blooded animal is a ruminant.

11. The method according to claim 7 wherein said pour-on formulation is administered in a quantity of up to about 50 ml onto the skin surface of said animal.

12. The method according to claim 7 wherein said warm-blooded animal is a ruminant.

13. The method according to claim 8 wherein said pour-on formulation is administered in a quantity of up to about 50 ml onto the skin surface of said animal.

14. The method according to claim 8 wherein said warm-blooded animal is a ruminant.

15. A pour-on formulation comprising a solution of about 10-40% w/v triclabendazole or its pharmaceutically acceptable salt thereof substantially dissolved in a solvent system;
   about 0.5% w/v abamectin; and
   wherein the solvent system comprises a glycol ether and benzyl alcohol.

16. A pour-on formulation comprising a solution of at least 10% w/v triclabendazole or its pharmaceutically acceptable salt substantially dissolved in a solvent system,
   about 0.5% w/v of milbemycin, and
   wherein the solvent system comprises a glycol ether and benzyl alcohol.

17. A pour-on formulation comprising a solution of at least 10% w/v triclabendazole or its pharmaceutically acceptable salt substantially dissolved in a solvent system,
   about 0.5% w/v of abamectin, and
   wherein the solvent system comprises a glycol ether and benzyl alcohol.

18. The pour-on formulation according to claim 16 or 17, wherein the triclabendazole is present in an amount of about 30% w/v.

19. A method of treating parasites in warm-blooded animals comprising administering to said animal in need thereof an effective amount of a pour-on formulation according to of claim 16 or 17.

20. A method of treating liver flukes in warm-blooded animals comprising administering to said animal in need thereof an effective amount of a pour-on formulation according to claim 16 or 17.

21. A method of treating fasciolosis in warm-blooded animals comprising administering to said animal in need thereof an effective amount of a pour-on formulation according to claim 16 or 17.

22. The method according to claim 20 wherein said pour-on formulation is administered in a quantity of up to about 50 ml onto the skin surface of said animal.

23. The method according to claim 20 wherein said warm-blooded animal is a ruminant.

24. The method according to claim 21 wherein said pour-on formulation is administered in a quantity of up to about 50 ml onto the skin surface of said animal.

25. The method according to claim 21 wherein said warm-blooded animal is a ruminant.

26. The method according to claim 20 wherein said pour-on formulation is administered in a quantity of up to about 50 ml onto the skin surface of said animal.

27. The method according to claim 20 wherein said warm-blooded animal is a ruminant.

* * * * *